(12) United States Patent
Putman

(10) Patent No.: US 7,196,088 B2
(45) Date of Patent: Mar. 27, 2007

(54) SUBSTITUTED TETRAHYDROISOQUINOLINES AND USES THEREOF

(75) Inventor: David George Putman, Stow, MA (US)

(73) Assignee: Roche Palo Alto LLC, Palto Alto, CA (US)

( * ) Notice: Subject to any disclaimer, the term of this patent is extended or adjusted under 35 U.S.C. 154(b) by 214 days.

(21) Appl. No.: 10/791,578

(22) Filed: Mar. 2, 2004

(65) Prior Publication Data

US 2004/0180874 A1    Sep. 16, 2004

Related U.S. Application Data

(60) Provisional application No. 60/451,516, filed on Mar. 3, 2003.

(51) Int. Cl.
*A61K 31/496* (2006.01)
*C07D 401/04* (2006.01)

(52) U.S. Cl. .................. 514/253.05; 544/363; 540/575; 546/141; 514/218; 514/309

(58) Field of Classification Search .............. 544/363; 514/253.05
See application file for complete search history.

(56) References Cited

U.S. PATENT DOCUMENTS

| | | |
|---|---|---|
| 5,665,723 A | 9/1997 | Hartman et al. |
| 5,719,144 A | 2/1998 | Hartman et al. |
| 6,011,050 A | 1/2000 | Muller et al. |
| 6,020,358 A | 2/2000 | Muller et al. |
| 6,417,362 B1 | 7/2002 | Ohkura et al. |
| 2004/0024210 A1 | 2/2004 | Johanssen et al. |

FOREIGN PATENT DOCUMENTS

| | | |
|---|---|---|
| EP | 0 189 612 B1 | 11/1992 |
| EP | 1 180 514 A1 | 2/2002 |
| EP | 0 635 492 B1 | 10/2002 |
| WO | WO 94/13659 A1 | 6/1994 |
| WO | WO 96/26187 A1 | 8/1996 |
| WO | 98/54135 | * 12/1998 |
| WO | WO 00/61556 A1 | 10/2000 |
| WO | WO 02/059107 A1 | 8/2002 |

* cited by examiner

*Primary Examiner*—Emily Bernhardt
(74) *Attorney, Agent, or Firm*—Robert C. Hall

(57) ABSTRACT

The invention provides compounds of the formula:

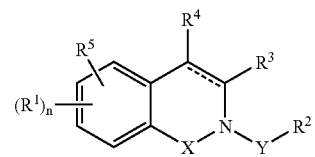

and pharmaceutically acceptable salts or prodrugs thereof, wherein, n, X, Y, $R^1$, $R^2$, $R^3$, $R^4$ and $R^5$ are as defined herein. The subject compounds are useful for treatment of 5-HT6 receptor antagonist-mediated diseases. Also provides are methods for preparing, compositions comprising, and methods for using the subject compounds.

17 Claims, No Drawings

SUBSTITUTED TETRAHYDROISOQUINOLINES AND USES THEREOF

CROSS REFERENCE

This application claims the benefit of priority of U.S. Provisional Patent Application Ser. No. 60/451,516, filed Mar. 3, 2003, which is incorporated herein by reference in its entirety.

FIELD OF THE INVENTION

This invention relates to substituted tetrahydroisoquinoline and isoquinoline compounds, and associated compositions, methods for use as therapeutic agents, and methods of preparation thereof.

BACKGROUND OF THE INVENTION

The actions of the neurotransmitter 5-hydroxytryptamine (5-HT) as a major modulatory neurotransmitter in the brain, are mediated through a number of receptor families termed 5-HT1, 5-HT2, 5-HT3, 5-HT4, 5-HT5, 5-HT6, and 5-HT7. Based on a high level of 5-HT6 receptor mRNA in the brain, it has been stated that the 5-HT6 receptor may play a role in the pathology and treatment of central nerve system disorders. In particular, 5-HT6 selective ligands have been identified as potentially useful in the treatment of certain CNS disorders such as Parkinson's disease, Huntington's disease, anxiety, depression, manic depression, psychoses, epilepsy, obsessive compulsive disorders, migraine, Alzheimer's disease (enhancement of cognitive memory), sleep disorders, feeding disorders such as anorexia and bulimia, panic attacks, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain gastrointestinal (GI) disorders such as functional bowel disorder. See for example, B. L. Roth et al., *J. Pharmacol. Exp. Ther.*, 1994, 268, pages 1403–14120, D. R. Sibley et al., *Mol. Pharmacol.*, 1993, 43, 320–327, A. J. Sleight et al., *Neurotransmission*, 1995, 11, 1–5, and A. J. Sleight et al., *Serotonin ID Research Alert*, 1997, 2(3), 115–8.

While some 5-HT6 modulators have been disclosed, there continues to be a need for compounds that are useful for modulating 5-HT6.

SUMMARY

The invention provides compounds of the formula I:

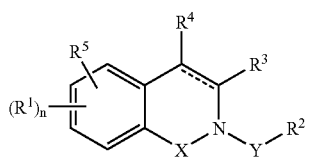

and pharmaceutically acceptable salts or prodrugs thereof, wherein:
n is from 0 to 3;
X is —$CR^aR^b$— or —C(O)—, wherein $R^a$ and $R^b$ each independently are hydrogen or alkyl;
---- is an optional bond;
Y is —$SO_2$— when X is —$CR^aR^b$— and Y is —$CR^cR^d)_p$— when X is —C(O)—, wherein p is from 1 to 3 and $R^c$ and $R^d$ each independently are hydrogen or alkyl;
each $R^1$ independently is halo, alkyl, haloalkyl, heteroalkyl, hydroxy, nitro, alkoxy, cyano, —$S(O)_q$—$R^e$, —$NR^eR^f$, —C(=O)—$NR^eR^f$, —$SO_2$—$NR^eR^f$, —$N(R^e)$—C(=O)—$R^f$, or —C(=O) $R^e$, wherein q is from 0 to 2 and $R^e$ and $R^f$ each independently are hydrogen or alkyl;
$R^2$ is aryl, heteroaryl or cycloalkyl;
$R^3$ and $R^4$ each independently are hydrogen or alkyl; and
$R^5$ is of the formula:

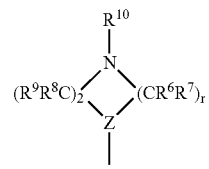

wherein:
r is from 1 to 3;
Z is —N— or —CH—; and
$R^6$, $R^7$, $R^8$, $R^9$ and $R^{10}$ each independently are hydrogen or alkyl.

The invention also provides methods for preparing the aforementioned compounds. One such method comprises:
reacting a compound of the formula:

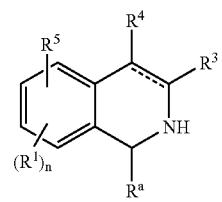

wherein:
n is from 0 to 3;
each $R^1$ independently is halo, alkyl, haloalkyl, heteroalkyl, hydroxy, nitro, alkoxy, cyano, —$S(O)_q$—$R^e$, —$NR^eR^f$, —C(=O)—$NR^eR^f$, —$SO_2$—$NR^eR^f$, —$N(R^e)$—C(=O)—$R^f$, or —C(=O) $R^e$, wherein q is from 0 to 2 and $R^e$ and $R^f$ each independently are hydrogen or alkyl;
$R^a$, $R^3$ and $R^4$ each independently are hydrogen or alkyl;
---- is an optional bond;
$R^5$ is of the formula:

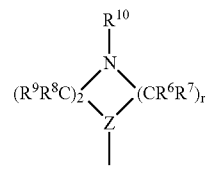

wherein:
r is from 1 to 3;
Z is —N— or —CH—; and $R^6$, $R^7$, $R^8$, $R^9$ and $R^{10}$ each independently are hydrogen or alkyl;

with a sulfonyl halide of the formula: $R^2$—$SO_2$-G wherein $R^2$ is aryl, heteroaryl or cycloalkyl and G is halo;

to yield a compound of the formula:

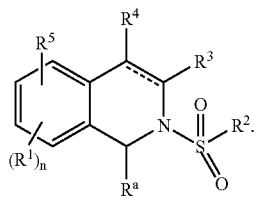

The invention further provides compositions comprising, and methods for using the aforementioned compounds.

DETAILED DESCRIPTION OF THE INVENTION

The invention provides substituted isoquinoline compounds, associated compositions, methods for use as therapeutic agents, and methods of preparation thereof. In specific embodiments the invention provides piperazinyl-substituted isoquinoline and isoquinolinone compounds and associated pharmaceutical compositions, and methods for using the same in the treatment of CNS diseases and gastrointestinal tract disorders. All publications noted herein are incorporated by reference herein in their entirety.

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" means a moiety of the formula —OR, wherein R is an alkyl moiety as defined herein. Examples of alkoxy moieties include, but are not limited to, methoxy, ethoxy, isopropoxy, and the like.

"Antagonist" refers to a compound that diminishes or prevents the action of another compound or receptor site.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, naphthalenyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Arylalkyl" and "Aralkyl", which may be used interchangeably, mean a radical —$R^aR^b$ where $R^a$ is an alkylene group and $R^b$ is an aryl group as defined herein; e.g., benzyl, phenylethyl, 3-(3-chlorophenyl)-2-methylpentyl, and the like are examples of arylalkyl.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof such as cyclohexenyl, cyclopentenyl, and the like.

"Cycloalkylalkyl" means a moiety of the formula —R'—R", where R' is alkylene and R" is cycloalkyl as defined herein.

"Heteroalkyl" means an alkyl radical as defined herein wherein one, two or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

The terms "halo" and "halogen", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —CH$_2$Cl, —CH$_2$CF$_3$, —CH$_2$CCl$_3$, perfluoroalkyl (e.g., —CF$_3$), and the like.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like, including partially unsaturated derivatives thereof.

"Optionally substituted", when used in association with "aryl", "phenyl", "naphthalenyl", "heteroaryl" or "heterocyclyl", means an aryl, phenyl, naphthalenyl, heteroaryl or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease state" means any disease, condition, symptom, or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like.

Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

The terms "pro-drug" and "prodrug", which may be used interchangeably herein, refer to any compound which releases an active parent drug according to formula I in vivo when such prodrug is administered to a mammalian subject. Prodrugs of a compound of formula I are prepared by modifying one or more functional group(s) present in the compound of formula I in such a way that the modification(s) may be cleaved in vivo to release the parent compound. Prodrugs include compounds of formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of formula I, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, see Bundegaard, H. "Design of Prodrugs" p 1–92, Elesevier, New York-Oxford (1985), and the like.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to chose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgement of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:
(i) preventing the disease state, i.e. causing the clinical symptoms of the disease state not to develop in a subject that may be exposed to or predisposed to the disease state, but does not yet experience or display symptoms of the disease state.
(ii) inhibiting the disease state, i.e., arresting the development of the disease state or its clinical symptoms, or
(iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature used in this Application is based on AUTONOM™ v.4.0, a Beilstein Institute computerized system for the generation of IUPAC systematic nomenclature. For convenience, the IUPAC numbering of the positions of representative isoquinoline compounds described herein is shown by the formula:

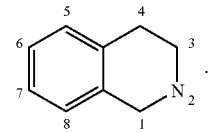

The chemical structures shown herein were prepared using ISIS® Version 2.2. Any open valency on a carbon, nitrogen or oxygen in the structures herein indicates the presence of a hydrogen.

Compounds of the Invention

The invention provides compounds of the formula I:

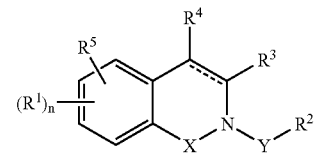

and pharmaceutically acceptable salts or prodrugs thereof, wherein:

n is from 0 to 3; preferably m is 0 or 1;

X is —$CR^aR^b$— or —C(O)—, wherein $R^a$ and $R^b$ each independently are hydrogen or alkyl; preferably X is —$CR^aR^b$— and $R^a$ and $R^b$ are hydrogen;

---- is an optional bond;

Y is —$SO_2$— when X is —$CR^aR^b$— and Y is —$(CR^c R^d)_p$— when X is —C(O)—, wherein p is from 1 to 3 and $R^c$ and $R^d$ each independently are hydrogen or alkyl; preferably p is 1 and $R^c$ and $R^d$ are hydrogen;

each $R^1$ independently is halo, alkyl, haloalkyl, heteroalkyl, hydroxy, nitro, alkoxy, cyano, —$S(O)_q$—$R^e$, —$NR^eR^f$, —C(=O)—$NR^eR^f$, —$SO_2$—$NR^eR^f$, —N($R^e$)—C(=O)—$R^f$, or —C(=O) $R^e$, wherein q is from 0 to 2 and $R^e$ and $R^f$ each independently are hydrogen or alkyl; preferably $R^1$ is halo, alkyl or alkoxy;

$R^2$ is aryl, heteroaryl or cycloalkyl; preferably $R^2$ is aryl or heteroaryl; more preferably, $R^2$ is optionally substitute phenyl or optionally substituted napthalenyl, such as phenyl, 2-halophenyl, 3-halopheny, 4-halophenyl, 2,3-dihalophenyl, 2,4-dihalophenyl, 3,4-dihalophenyl, 2,5-dihalophenyl, 3,5-dihalophenyl, 2,6-dihalophenyl, 2-haloalkylphenyl, 3-haloalkylpheny, 4-haloalkylphenyl, 2,3-dihaloalkylphenyl, 2,4-dihaloalkylphenyl, 3,4-dihaloalkylphenyl, 2,5-dihaloalkylphenyl, 3,5-dihaloalkylphenyl, 2,6-dihaloalkylphenyl, 2-alkoxyphenyl, 3-alkoxypheny, 4-alkoxyphenyl, 2,3-dialkoxyphenyl, 2,4-dialkoxyphenyl, 3,4-dialkoxyphenyl, 3,5-dialkoxyphenyl, 2,5-dialkoxyphenyl, 2,6-dialkoxyphenyl, 2-alkylphenyl, 3-alkylphenyl, 4-alkylphenyl, 2,3-dialkylphenyl, 2,4-dialkylphenyl, 3,4-dialkylphenyl, 3,5-dialkylphenyl, 2,5-dialkylphenyl, 2,6-dialkylphenyl, naphthalene-1-yl, napthalene-2-yl and the like;

$R^3$ and $R^4$ each independently are hydrogen or alkyl; preferably $R^3$ and $R^4$ are hydrogen; and $R^5$ is a heterocyclyl of the formula:

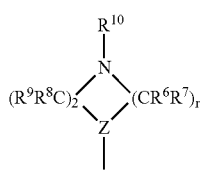

wherein:

Z is —N— or —CH—; preferably Z is —N—;

r is from 1 to 3; preferably r is 2; and $R^6$, $R^7$, $R^8$, $R^9$ and $R^{10}$ each independently are hydrogen or alkyl; preferably $R^6$, $R^7$, $R^8$, $R^9$ and $R^{10}$ are hydrogen.

Where any of $R^1$, $R^3$, $R^4$, $R^6$, $R^7$, $R^8$, $R^9$, $R^{10}$, $R^a$, $R^b$, $R^c$, $R^d$, $R^e$ and $R^f$ are alkyl, they are preferably lower alkyl, i.e. $C_1$–$C_6$alkyl, and more preferably $C_1$–$C_4$alkyl.

It should be understood that the scope of this invention encompasses not only the various isomers which may exist but also the various mixture of isomers which may be formed. Furthermore, the scope of the present invention also encompasses solvates and salts of compounds of formula I.

In certain embodiments, $R^2$ may be phenyl, 2-fluorophenyl, 3-fluorophenyl, 4-fluorophenyl, 2-chlorophenyl, 3-chlorophenyl, 3-methylphenyl, 4-methoxyphenyl, 2-methanesulfonylphenyl, 4-amidophenyl, 4-ureaphenyl, 3,5-dichlorophenyl, 2,3-dichlorophenyl, 2,5-dichlorophenyl, 3,5-di(trifluoromethyl)phenyl, 2,5-dimethoxyphenyl, 3-chloro-4-fluorophenyl, 2-chloro-4-fluorophenyl, naphthalen-1-yl, naphthalen-2-yl, or quinolin-8-yl.

In many embodiments of the invention, $R^5$ is at the 5-position or 6-position of the isoquinoline ring system, and more preferably at the 5-position, such that compounds of formula I may be represented by the formula II:

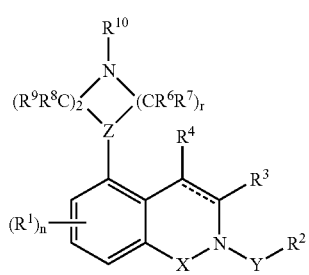

wherein n, r, X, Y, Z, $R^1$, $R^2$, $R^3$, $R^4$, $R^6$, $R^7$, $R^8$, $R^9$ and $R^{10}$ are as defined herein.

In certain embodiments, r is 2 and Z is nitrogen, such that $R^5$ is an optionally substituted piperazinyl group. In such embodiments, compounds of formula I may be represented by the formula III:

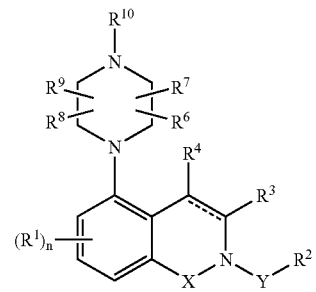

wherein n, X, Y, $R^1$, $R^2$, $R^3$, $R^4$, $R^6$, $R^7$, $R^8$, $R^9$ and $R^{10}$ are as defined herei In some presently preferred embodiments, compounds of formula I may more specifically be of the formula IV:

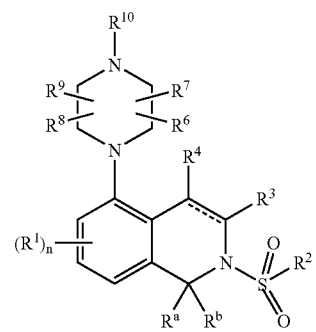

wherein n, $R^1$, $R^2$, $R^3$, $R^4$, $R^6$, $R^7$, $R^8$, $R^9$, $R^{10}$, $R^a$ and $R^b$ are as defined herein. In other preferred embodiments, compounds of formula I are of the formula V:

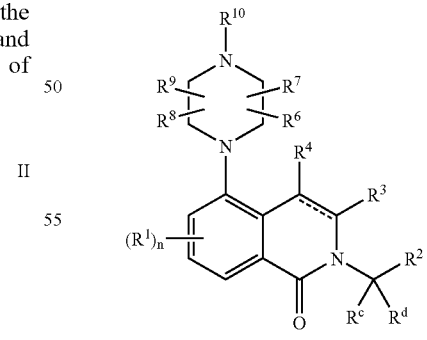

wherein n, $R^1$, $R^2$, $R^3$, $R^4$, $R^6$, $R^7$, $R^8$, $R^9$, $R^{10}$, $R^c$ and $R^d$ again are as defined herein.

Representative compounds in accordance with the invention are shown in Table 1, together with the experimental examples (described below) used in preparation of the compounds and associated mass spectroscopy M+H.

TABLE 1

| | Name (Autonom ®) | Structure | Example | M + H |
|---|---|---|---|---|
| 1 | 2-Benzenesulfonyl-5-(4-methylpiperazin-1-yl)-1,2,3,4-tetra-hydroisoquinoline | 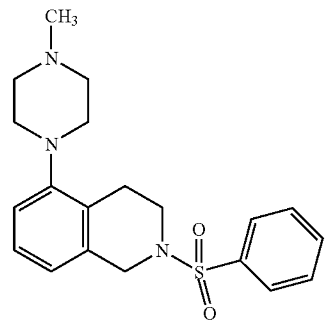 | 1 | 371 |
| 2 | 2-Benzenesulfonyl-5-piperazin-1-yl-1,2,3,4-tetra-hydroisoquinoline | 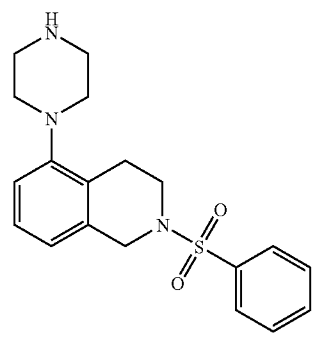 | 1 | 356 |
| 3 | 2-(4-Fluoro-benzenesulfonyl)-5-piperazin-1-yl-1,2,3,4-tetra-hydroisoquinoline | 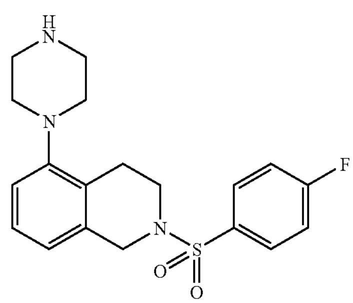 | 1 | 374 |
| 4 | 2-(4-Methoxy-benzenesulfonyl)-5-piperazin-1-yl-1,2,3,4-tetra-hydroisoquinoline | 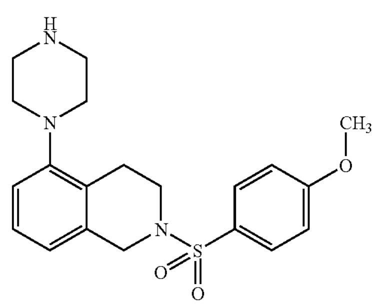 | 1 | 387 |
| 5 | 2-(3-Fluoro-benzenesulfonyl)-5-piperazin-1-yl-1,2,3,4-tetra-hydroisoquinoline | 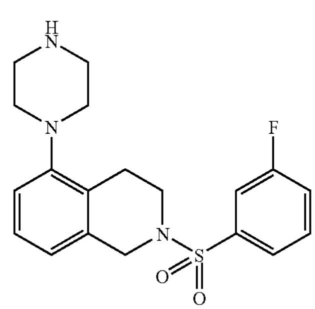 | 1 | 374 |

TABLE 1-continued

| | Name (Autonom ®) | Structure | Example | M + H |
|---|---|---|---|---|
| 6 | 2-(3,5-Dichloro-benzenesulfonyl)-5-piperazin-1-yl-1,2,3,4-tetrahydroisoquinoline | 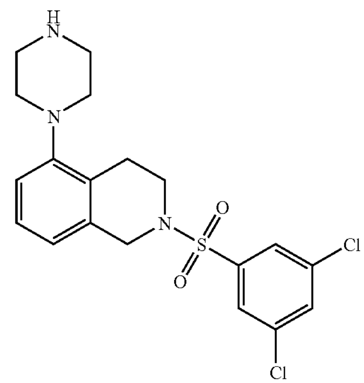 | 1 | 425 |
| 7 | 2-(3,5-Bis-trifluoromethyl-benzenesulfonyl)-5-piperazin-1-yl-1,2,3,4-tetrahydroisoquinoline | 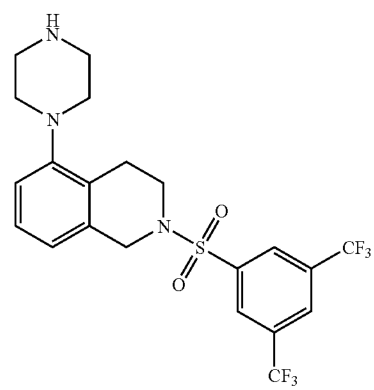 | 1 | 492 |
| 8 | 2-(Naphthalene-1-sulfonyl)-5-piperazin-1-yl-1,2,3,4-tetrahydroisoquinoline | 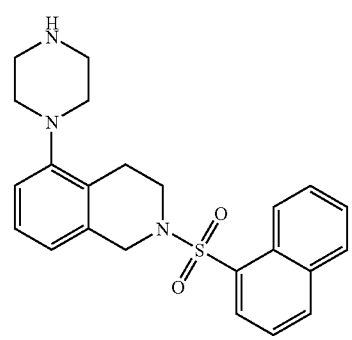 | 1 | 407 |
| 9 | 2-(Naphthalene-2-sulfonyl)-5-piperazin-1-yl-1,2,3,4-tetrahydroisoquinoline | 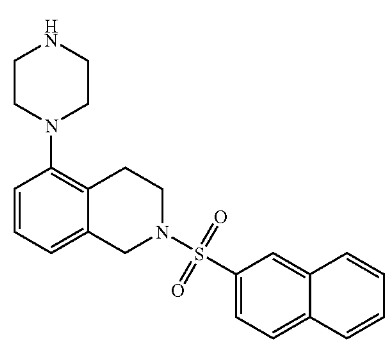 | 1 | 407 |

TABLE 1-continued

| | Name (Autonom ®) | Structure | Example | M + H |
|---|---|---|---|---|
| 10 | 2-(2,5-dimethoxy-benzenesulfonyl)-5-piperazin-1-yl-1,2,3,4-tetrahydroisoquinoline | 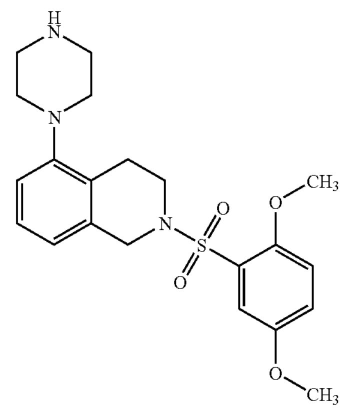 | 1 | 417 |
| 11 | 2-(3-Chloro-4-fluoro-benzenesulfonyl)-5-piperazin-1-yl-1,2,3,4-tetrahydroisoquinoline | 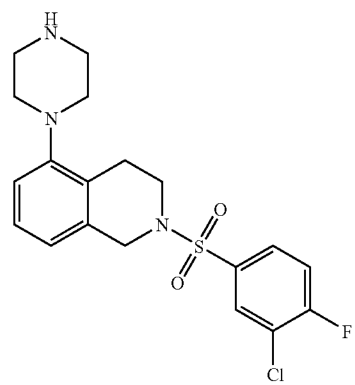 | 1 | 409 |
| 12 | 2-(2-Fluoro-benzenesulfonyl)-5-piperazin-1-yl-1,2,3,4-tetrahydroisoquinoline | 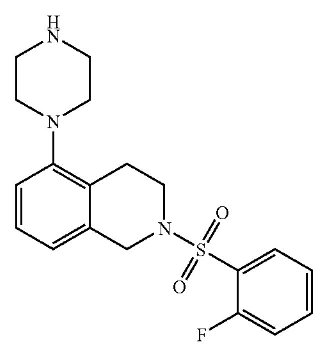 | 1 | 374 |
| 13 | 2-(2-Chloro-benzenesulfonyl)-5-piperazin-1-yl-1,2,3,4-tetrahydroisoquinoline | 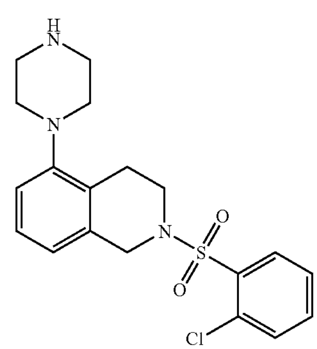 | 1 | 391 |

TABLE 1-continued

| | Name (Autonom ®) | Structure | Example | M + H |
|---|---|---|---|---|
| 14 | 2-(3-Chloro-benzenesulfonyl)-5-piperazin-1-yl-1,2,3,4-tetra-hydroisoquinoline | 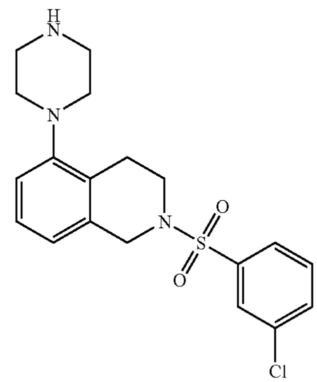 | 1 | 391 |
| 15 | 2-(3-Methyl-benzenesulfonyl)-5-piperazin-1-yl-1,2,3,4-tetra-hydroisoquinoline | 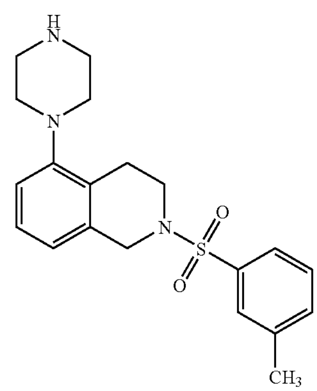 | 1 | 371 |
| 16 | 2-(2,3-Dichloro-benzenesulfonyl)-5-piperazin-1-yl-1,2,3,4-tetra-hydroisoquinoline | 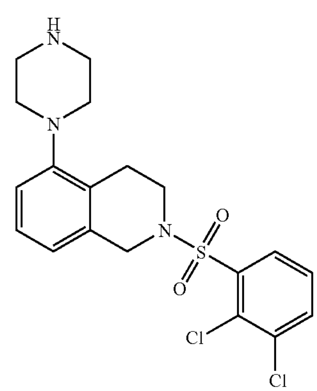 | 1 | 425 |
| 17 | 2-(2-Chloro-4-fluoro-benzenesulfonyl)-5-piperazin-1-yl-1,2,3,4-tetra-hydroisoquinoline | 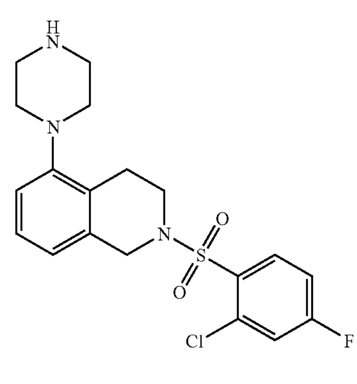 | 1 | 409 |

TABLE 1-continued

| Name (Autonom ®) | Structure | Example | M + H |
|---|---|---|---|
| 18 2-(2,5-Dichloro-benzenesulfonyl)-5-piperazin-1-yl-1,2,3,4-tetrahydroisoquinoline | | 1 | 425 |
| 19 2-Benzyl-5-piperazin-1-yl-3,4-dihydro-2H-isoquinolin-1-one | | 2 | 322 |
| 20 2-Benzyl-5-(4-ethyl-piperazin-1-yl)-3,4-dihydro-2H-isoquinolin-1-one | | 2 | 350 |
| 21 2-(2-Methanesulfonyl-benzenesulfonyl)-5-piperazin-1-yl-1,2,3,4-tetrahydroisoquinoline | | 1 | 357 |

TABLE 1-continued

| | Name (Autonom ®) | Structure | Example | M + H |
|---|---|---|---|---|
| 22 | 3-(5-Piperazin-1-yl-3,4-dihydro-1H-iso-quinoline-2-sulfonyl)-benzamide | 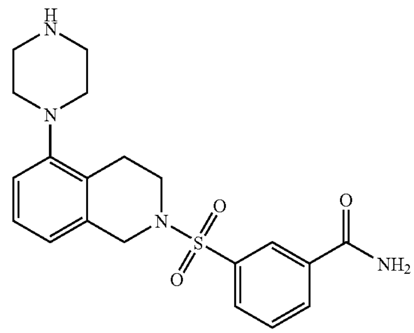 | 1 | 401 |
| 23 | [2-(5-Piperazin-1-yl-3,4-dihydro-1H-iso-quinoline-2-sulfonyl)-phenyl]-urea | 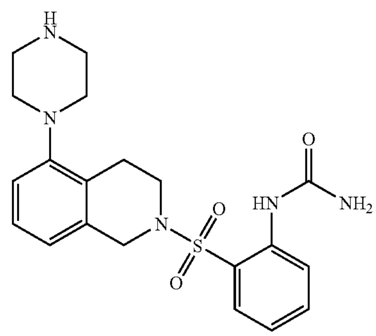 | 1 | 417 |
| 24 | 8-(5-Piperazin-1-yl-3,4-dihydro-1H-iso-quinoline-2-sulfonyl)-quinoline | 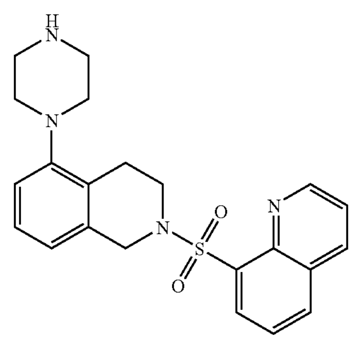 | 1 | 410 |

Another aspect of the invention provides a composition comprising a therapeutically effective amount of at least one compound of formula I and a pharmaceutically acceptable carrier.

Yet another aspect of the invention provides a method for treating a central nervous system (CNS) disease state in a subject comprising administering to the subject a therapeutically effective amount of a compound of formula I. The disease state may comprise, for example, psychoses, schizophrenia, manic depressions, neurological disorders, memory disorders, attention deficit disorder, Parkinson's disease, amyotrophic lateral sclerosis, Alzheimer's disease or Huntington's disease.

Still another aspect of the present invention provides a method for treating a disorder of the gastrointestinal tract in a subject comprising administering to the subject a therapeutically effective amount of a compound of formula I.

Another aspect of the present invention provides a method for producing a compound of formula I.

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1–15; *Rodd's Chemistry of Carbon Compounds*, Elsevier Science Publishers, 1989, Volumes 1–5 and Supplementals; and *Organic Reactions*, Wiley & Sons: New York, 1991, Volumes 1–40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A below illustrates one synthetic procedure usable to prepare specific compounds of formula I, wherein G is halo or other leaving group, and n, r, $R^1$, $R^2$, $R^3$, $R^4$, $R^6$, $R^7$, $R^8$, $R^9$, $R^{10}$ and $R^a$ are as defined herein.

SCHEME A

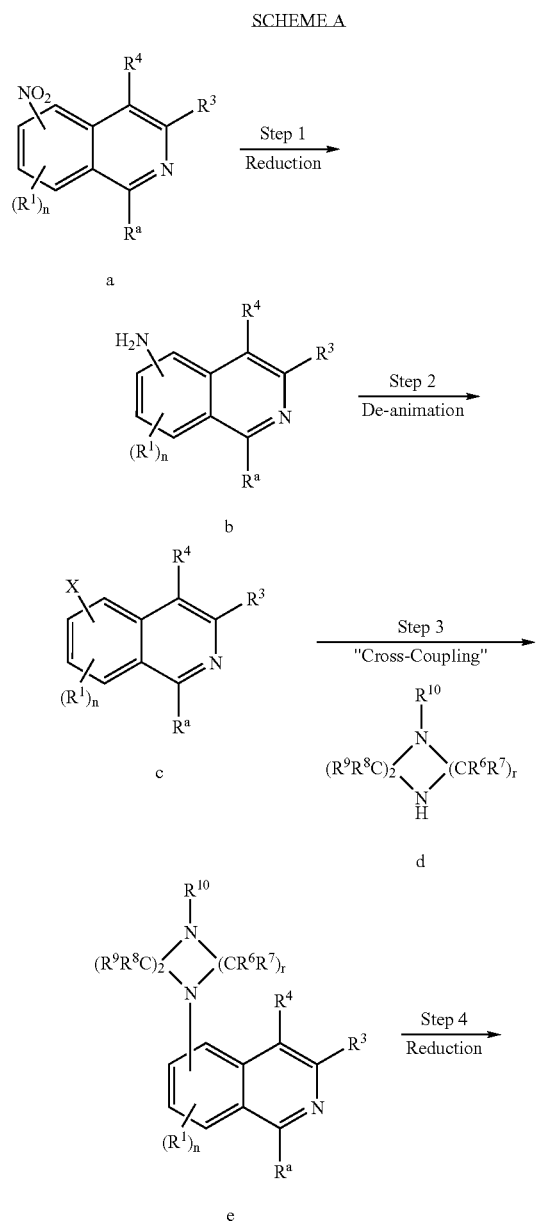

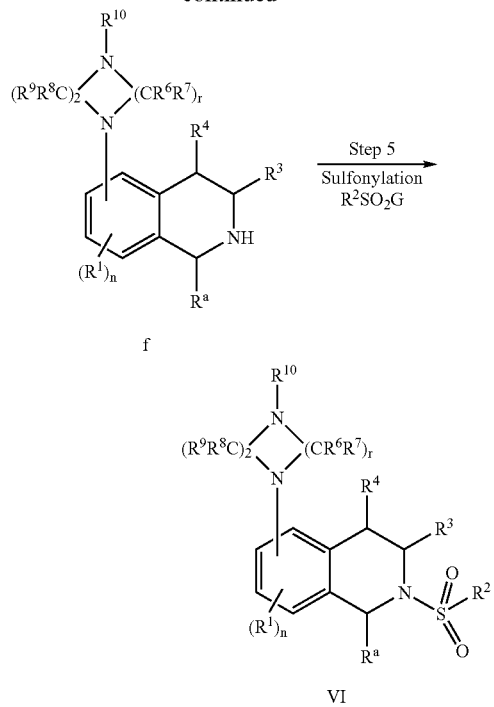

In Step 1 of Scheme A, a nitroisoquinoline a is reduced to an aminoisoquinoline b. This selective nitro reduction may be carried out under relatively mild conditions using $H_2$ in the presence of a Pd or Pt catalyst. Various nitro-substituted isoquinolines usable in this step are commercially available or can be prepared via well known techniques.

In Step 2 a deamination reaction is carried out in the presence of acid HX and copper powder under aqueous, oxidizing conditions to provide a substituted isoquinoline c wherein X is halo, preferably bromo or chloro. Various amino-substituted isoquinolines are commercially available or can be prepared via well known techniques for use in this step.

In Step 3, a cross-coupling reaction is utilized in which the substituted isoquinoline c is treated with a heterocyclic amine d in the presence of a palladium catalyst to yield a heterocyclyl-substituted isoquinoline e. This cross-coupling reaction may be achieved with heating under nonpolar solvent conditions. Where $R^{10}$ is hydrogen, BOC protection or other removable protection strategies may be used to protect the exposed nitrogen of heterocyclic amine d. This cross-coupling amination reaction is described in *An Improved Catalyst System For Aromatic Carbon-Nitrogen Bond Formation: The Possible Involvement Of Bis(Phosphine) Palladium Complexes As Key Intermediates*. Wolfe et al., *J. Am. Chem. Soc.* ($^{1996}$), 118(30), 7215–7216.

The heterocyclyl-substituted isoquinoline e of Step 3 is optionally reduced in Step 4 to provide a heterocyclyl-substituted tetrahydroisoquinoline f. The reduction of Step 4 may be achieved using excess borane under polar aprotic solvent conditions.

In Step 5, the heterocyclyl-substituted tetrahydroisoquinoline f of Step 4 is treated with a sulfonyl halide $R^2SO_2G$ to provide a sulfonylated, heterocyclyl-substituted tetrahydroisoquinoline VI, wherein $R^2$ is aryl, heteroaryl or cycloalkyl as described above. Numerous aryl, heteroaryl and cycloalkyl sulfonyl chlorides and bromides are commercially available or are readily prepared, and may be used with the well-known Schotten-Baumann procedure (Et$_2$O/aqueous K$_2$CO$_3$) in Step 5 to form the sulfonylated heterocyclyl-substituted tetrahydroisoquinoline VI.

The tetrahydroisoquinoline VI of Scheme A is of the formula I discussed above and represents a more specific case wherein Z is N, X is —CR$^a$R$^b$— with R$^b$ shown as hydrogen, and with Y being —SO$_2$—. In many embodiments the heterocyclic amine d utilized in Scheme A may be a piperazine of the formula:

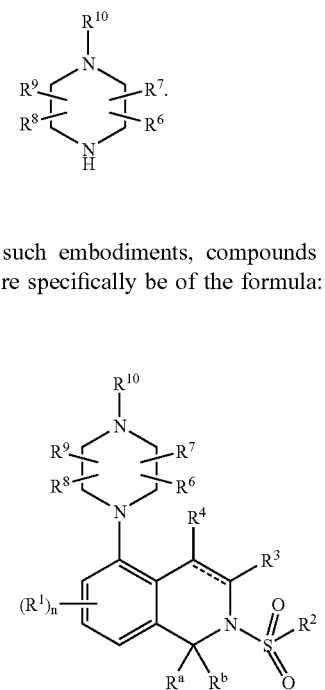

In such embodiments, compounds of formula VI would more specifically be of the formula:

described above (with R$^b$ being shown as hydrogen in formula VI).

Many variations on the procedure of Scheme A are possible and will suggest themselves to those skilled in the art upon review of this disclosure. For example, the heterocyclyl-substituted isoquinoline e may be prepared directly by reaction of nitrogen mustard (bis-(2-chloroethyl)-amine) with the amine b, with Steps 2 and 3 of Scheme A being omitted. The reaction of nitrogen mustard with amines to form heterocycles in this manner is well known in the art. The carbon at position 1 of the tetrahydroisoquinoline VI is benzylic in nature and subject to relatively facile alkylation, and thus in another variation of Scheme A, an alkyl group Rb may be introduced at position 1 using conventional synthetic techniques. Similarly, position 4 of the tetrahydroisoquinoline VI may be subject to alkylation if desired. Additionally, the location and chemical nature of the R$^1$ groups may in some embodiments be selected to facilitate the cross coupling reaction of Step 3.

Specific compounds of formula I may also be prepared via the procedure shown in Scheme B, wherein G is halo or other leaving group and n, q, R$^1$, R$^2$, R$^3$, R$^4$, R$^6$, R$^7$, R$^8$, R$^9$, R$^{10}$ and R$^a$ are as defined herein.

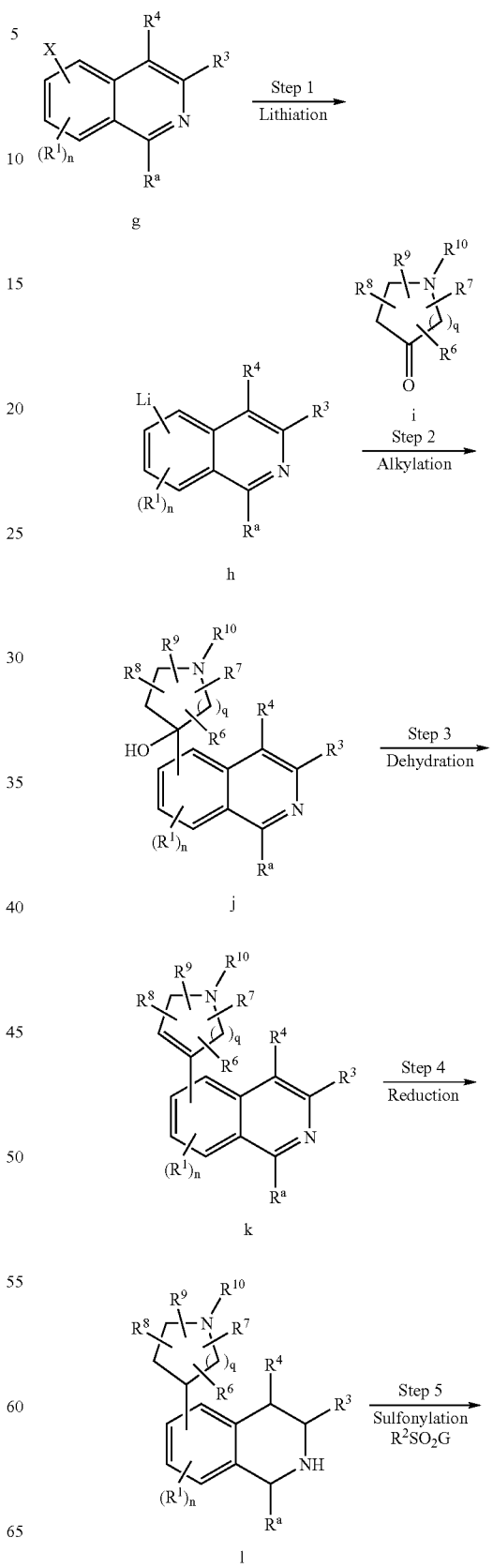

SCHEME B

-continued

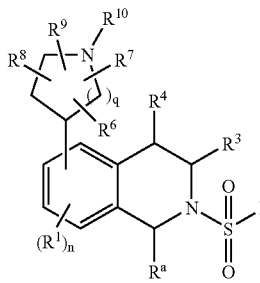

VII

In Step 1 of Scheme B, the halo-substituted isoquinoline E is treated with an alkyllithium reagent or other strong base under anhydrous polar aprotic conditions and dry ice/acetone temperature to generate a lithiated isoquinoline h. The lithiated isoquinoline h is not isolated but is used directly in Step 2.

An alkylation is effected in Step 2 by introducing a heterocyclic ketone i to the lithiated isoquinoline h to provide a heterocyclyl-substituted isoquinoline j. The heterocyclic ketone i may comprise, for example, pyrrolidone (q=1) or piperidone (q=2), both of which are commercially available. Many substituted pyrrolidinones and piperidinones are also commercially available or are readily prepared via known synthetic routes, and may be used in this step. Where $R^{10}$ is hydrogen, BOC protection or other removable protection strategies may be used to protect the exposed nitrogen of heterocyclic ketone i and corresponding nitrogen on the heterocyclyl-substituted isoquinoline j.

In Step 3, the heterocyclyl-substituted isoquinoline j prepared in Step 2 is dehydrated by treatment with mild acid to yield a heterocyclyl-substituted isoquinoline k wherein the heterocyclyl moiety is partially unsaturated.

In Step 4, the heterocyclyl-substituted isoquinoline k of Step 3 is reduced to provide a heterocyclyl-substituted tetrahydroisoquinoline l. This reduction may be achieved via hydrogenation using a platinum or palladium catalyst under mild ethanolic conditions.

In Step 5, the heterocyclyl-substituted tetrahydroisoquinoline l of Step 4 is sulfonylated, using the sulfonyl halide $R^2SO_2G$ in the manner described above for Scheme A, to provide a heterocyclyl-substituted, sulfonylated tetrahydroisoquinoline VII in accordance with the invention. Sulfonyl halide g may comprise, for example, an arylsulfonyl halide, a heteroarylsulfonylhalide, or a cycloalkylsulfonyl halide. The compound of formula VII represents a compound of formula I, discussed above, in the specific case wherein Z is —CH—, X is —$CR^aR^b$— with $R^b$ shown as hydrogen, and Y is —$SO_2$—.

As in the case of Scheme A discussed above, variations on the synthetic procedures of Scheme B are possible and will be readily apparent to those skilled in the art. In one such variation, for example, reduction of the isoquinoline ring may be carried out selectively, leaving the unsaturation present in the heterocyclyl moiety. In another variation, the unsaturation in the heterocyclyl moiety may be selectively reduced without reduction of the isoquinoline ring system. In certain embodiments, the dehydration event of Step 3 may occur spontaneously, in situ following the alkylation of Step 2, and in such embodiments Step 3 may be omitted.

In other embodiments of the invention, specific compounds of formula I may be prepared according to the procedure shown in Scheme C, wherein, G is a leaving group, preferably halo, and may be the same or different in each occurrence, R is any lower alkyl, preferably methyl, and may be the same or different in each occurrence, and n, $R^1$, $R^2$, $R^3$, $R^4$, $R^6$, $R^7$, $R^8$, $R^9$, $R^{10}$, $R^c$ and $R^d$ are as defined herein.

SCHEME C

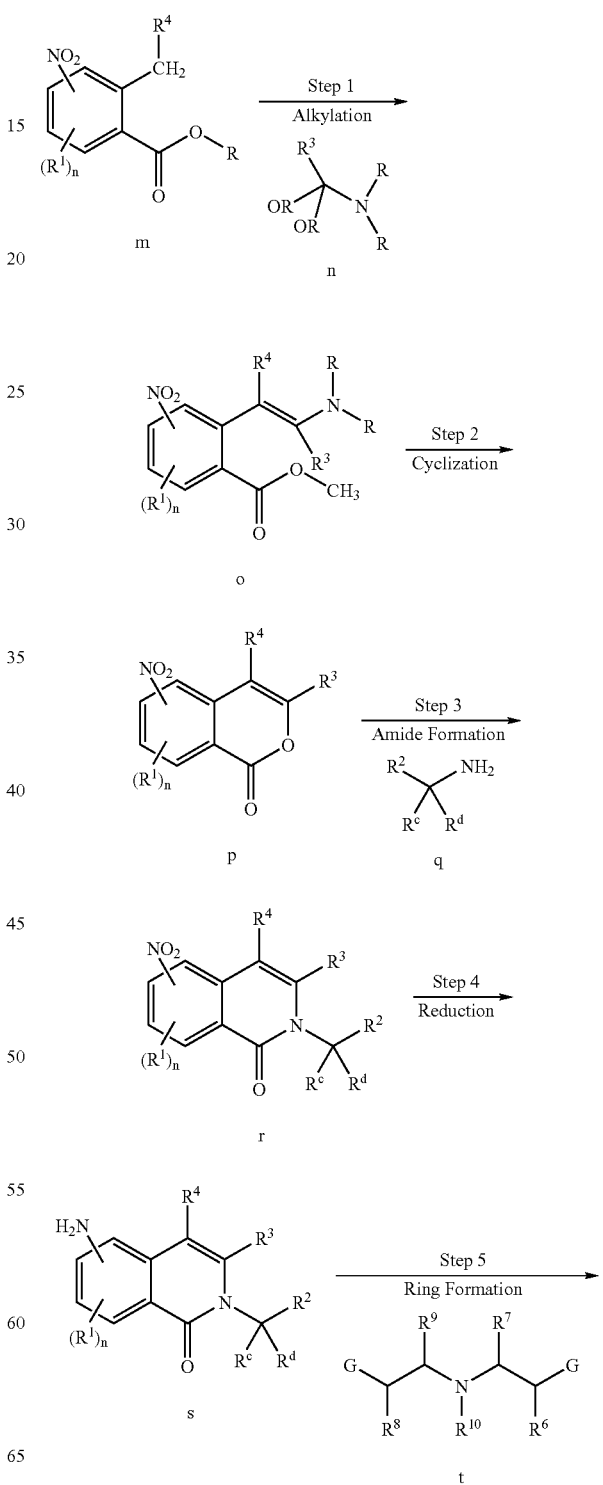

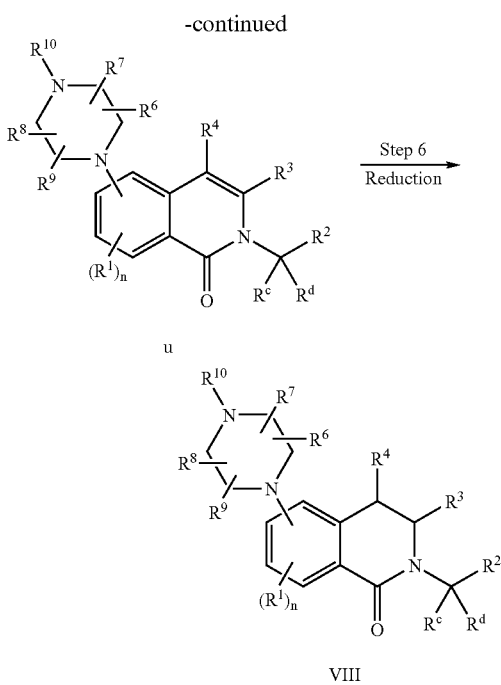

VIII

In Step 1 of Scheme C, alkylation of a 2-alkyl-nitrobenzoic acid ester m is carried out by reaction of the benzylic carbon of compound m with a "masked aldehyde" provided by an amide acetal n, with heating under mild basic conditions (Matsui et al., *J. Med. Chem.* 35, 18 (1992) 3307–3319), to provide an aldol condensation product o.

A cyclization of the aldol condensation product o is effected in Step 2 to provide a nitrobenzopyranone or nitroisochromone p. Cyclization may be achieved using silica as a catalyst by passing or eluting aldol condensation product o through silica using a hexane/ethyl acetate solvent system as described by Matsui et al., Supra.

In Step 3 amide formation occurs, and may be achieved by heating the nitrobenzopyranone p of Step 2 in the presence of amine q to provide a nitroisoquinolinone r. In many embodiments $R^2$ may be aryl or heteroaryl as noted above, such that amine q is benzylic in nature. Amine q may also be cyclohexylamine or other cycloalkylamine.

The nitro group of nitroisoquinolinone r is reduced in Step 4 to create a corresponding aminoisoquinolinone s. This reduction may be effected by hydrogenation using a platinum or palladium catalyst under mild conditions.

In Step 5 a ring formation occurs in which the aminoisoquinolinone s of Step 4 is reacted with a bis-haloalkylamine t to provide piperazinyl-substituted isoquinoline u. Bis-haloalkylamine t may comprise, for example, nitrogen mustard (G is Cl and $R^6$, $R^7$, $R^8$, $R^9$ and $R^{10}$ are hydrogen), and may be introduced to aminoisoquinolinone r as a hydrochloride salt. Where $R^{10}$ is hydrogen, BOC protection or other removable protection strategies may be used to protect the exposed nitrogen in subsequent steps.

The piperazinyl-substituted isoquinoline u of Step 5 is reduced in step 6 to provide a piperazinyl-substituted dihydroisoquinolinone VIII. This reduction may be achieved using excess borane under polar aprotic solvent conditions. In certain embodiments this reduction may be omitted such that the 3-position of the isoquinoline ring system remains unsaturated.

The piperazinyl-substituted dihydroisoquinolinone VIII represents a specific compound of formula I wherein X is —C(O)—, Y is —($CR^cR^d$)—, and Z is N. Many variations of the procedure illustrated in Scheme C may be used to provided other compounds of formula I in accordance with the invention. For example, a deamination of aminoisoquinolinone r in the manner described in Step 2 of Scheme A to yield a bromo-substituted isoquinoline (not shown), followed by the cross-coupling reaction of Step 3 of Scheme A and then reduction, provides an alternate route to the piperazinyl-substituted dihydroisoquinolinone VIII. Alternatively, such a bromo-substituted isoquinoline could be lithiated and then reacted with a heterocyclyl ketone as described in Steps 2 and 3 of Scheme B, to provide various heterocyclyl-substituted dihydroisoquinolinones in accordance with the invention. Other variations of Scheme C are also possible and are considered to be within the scope of this disclosure.

More specific details for producing compounds of formula I are described in the Examples section below.

Utility

The compounds of the invention have selective 5-HT6 receptor affinity and as such are expected to be useful in the treatment of certain central nervous system (CNS) disorders such as Parkinson's disease, Huntington's disease, anxiety, depression, manic depression, psychosis, epilepsy, obsessive compulsive disorders, migraine, Alzheimer's disease (enhancement of cognitive memory), sleep disorders, feeding disorders such as anorexia and bulimia, panic attacks, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain GI (gastrointestinal) disorders such functional bowel disorder.

Testing

The pharmacology of the compounds of this invention was determined by art recognized procedures. The in vitro techniques for determining the affinities of test compounds at the 5-HT6 receptor in radioligand binding and functional assays are described in Example 4.

Administration and Pharmaceutical Composition

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1–500 mg daily, preferably 1–100 mg daily, and most preferably 1–30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in the Examples below.

EXAMPLES

The following preparations and examples are given to enable those skilled in the art to more clearly understand and to practice the present invention. They should not be considered as limiting the scope of the invention, but merely as being illustrative and representative thereof.

Example 1

2-Benzenesulfonyl-5-piperazin-1-yl-1,2,3,4-tetrahydroisoquinoline

The synthetic procedures described in this Example were carried out according to the process shown in Scheme D.

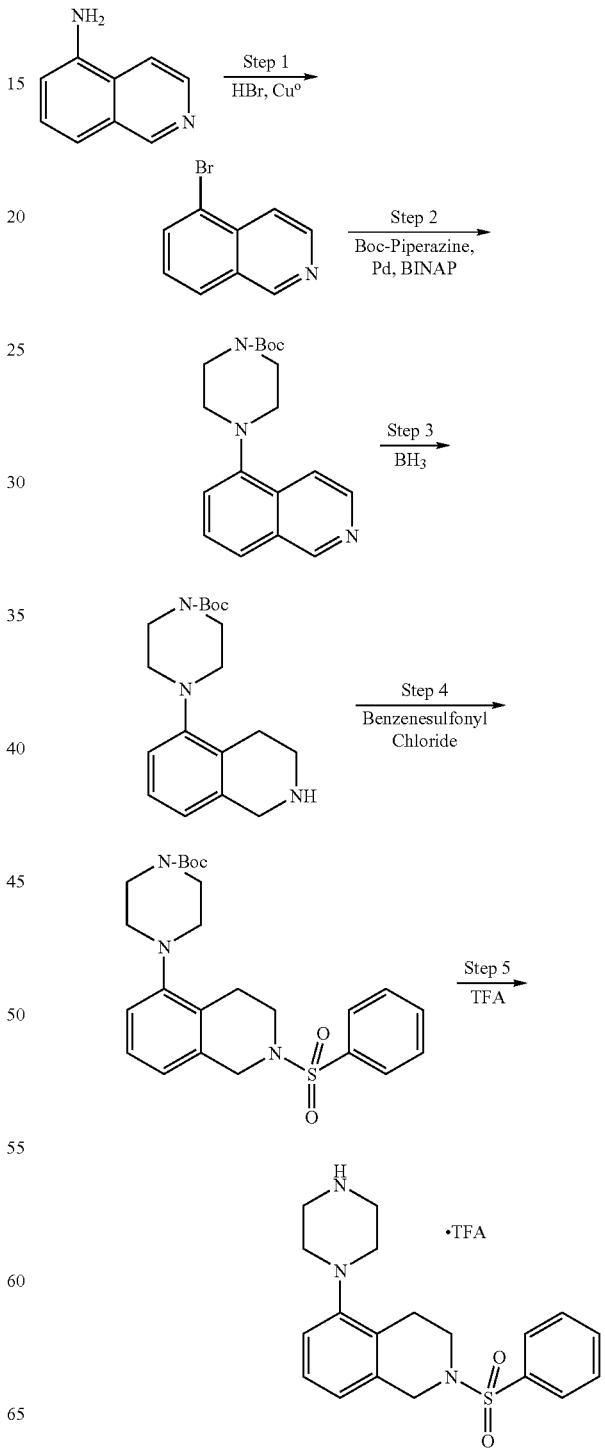

Step 1:

5-Bromoisoquinoline

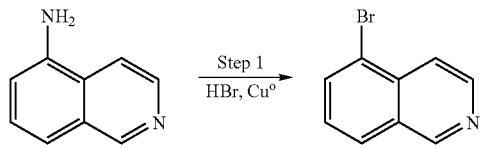

5-Aminoisoquinoline was purchased from Aldrich Chemical Co. (Cat. No. 13,610-7) and used in this step without purification. 5-Aminoisoquinoline (7.87 g was added to 100 mL of bromic acid (HBr) (48%) at −78° C. and stirred. To the stirred solution was added 4.74 g of sodium nitrate (NaNO$_3$) in portions. The mixture was allowed to stir for 1 hour at −78° C. following addition of the NaNO$_3$, after which 0.48 g of copper dust (Cu$^0$) was added. The reaction was allowed to warm to room temperature, and then was heated to 100° C. for one hour. The reaction mix was poured over ice and the resultant aqueous solution was basified to pH 14 by addition of sodium hydroxide (NaOH) (2M). The precipitated solids were collected and chromatographed to yield 2.4 g of 5-bromoisoquinoline as a white solid.

Step 2:

4-Isoquinoline-5-yl-piperazine-1-carboxylic acid tert-butyl ester

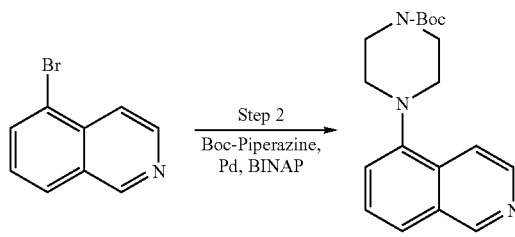

5-Bromoisoquinoline (1.37 g) from Step 1 was dissolved in 10 mL of toluene. To this solution was added palladium acetate (74 mg), rac-2,2'-bis(diphenylphosphino)-1,1'-binaphthyl (205 mg), 1-(tert-butoxycarbonyl)piperazine (1.29 g) and sodium tert-butoxide (885 mg). This reaction mixture was heated to 100° C. for 8 hours and then allowed to cool to room temperature. The cooled reaction mix was diluted with ethyl acetate (EtOAc) and washed with water, and the organic layer was separated, dried over magnesium sulfate (MgSO$_4$), and concentrated in vacuo. The resulting residue was chromatographed to yield 4-isoquinoline-5-yl-piperazine-1-carboxylic acid tert-butyl ester as 1.5 g of a white solid.

Step 3:

4-(1,2,3,4-tetrahydroisoquinolin-5-yl)-piperazine-1-carboxylic acid tert-butyl ester

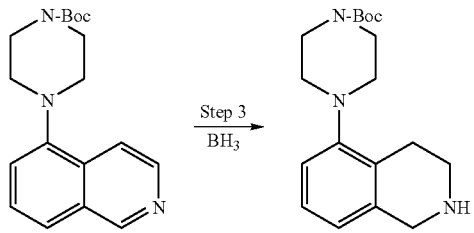

4-Isoquinoline-5-yl-piperazine-1-carboxylic acid tert-butyl ester (1.5 g) from Step 2 was dissolved in 5 mL of tetrahydrofuran (THF), and excess borane (BH$_3$) in THF was added thereto. The mixture was brought to reflux for 1 hour, and allowed to cool to room temperature. The mixture was then further cooled in an ice bath, and water was carefully added to the reaction mix to consume excess borane. The reaction mix was then diluted with EtOAc, washed with saturated aqueous sodium bicarbonate (NaHCO$_3$), dried over MgSO$_4$, and chromatographed to provide 4-(1,2,3,4-tetrahydroisoquinolin-5-yl)-piperazine-1-carboxylic acid tert-butyl ester as a viscous oil (0.668 g).

Step 4:

4-(2-benzenesulfonyl-1,2,3,4-tetrahydroisoquinolin-5-yl)-piperazine-1-carboxylic acid tert-butyl ester

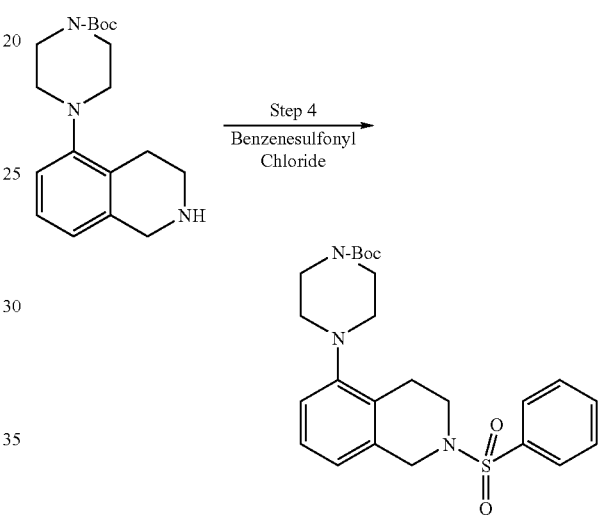

4-(1,2,3,4-Tetrahydroisoquinolin-5-yl)-piperazine-1-carboxylic acid tert-butyl ester as a viscous oil (150 mg) from Step 3 was reacted with benzenesulfonyl chloride (60 microliters) using the Schotten-Baumann procedure (50 mL diethyl ether (Et$_2$O) and 50 mL aqueous sodium carbonate). The ether layer was separated, dried over MgSO$_4$, and concentrated in vacuo. The residue was chromatographed to provide 1.76 mg of 4-(2-benzenesulfonyl-1,2,3,4-tetrahydroisoquinolin-5-yl)-piperazine-1-carboxylic acid tert-butyl ester as a white solid.

Step 5:

2-Benzenesulfonyl-5-piperazin-1-yl-1,2,3,4-tetrahydroisoquinoline

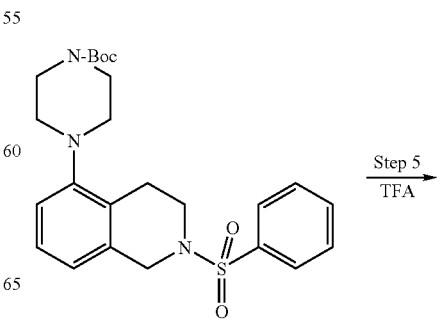

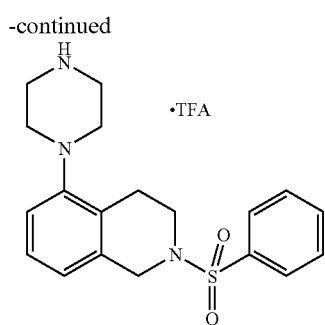

4-(2-Benzenesulfonyl-1,2,3,4-tetrahydroisoquinolin-5-yl)-piperazine-1-carboxylic acid tert-butyl ester (1.76 mg) from Step 5 was dissolved in 3 mL of trifluoroacetic acid (TFA) and heated briefly via steam bath. Excess TFA was removed in vacuo, and the residue was recrystallized from absolute ethanol to yield 83 mg of 2-Benzenesulfonyl-5-piperazin-1-yl-1,2,3,4-tetrahydroisoquinoline trifluoroacetic acid salt as a white solid, MP=214–216° C., MS M+H=358.

Using a procedure similar to that described above, and replacing the benzenesulfonyl chloride of Step 4 with the appropriate substituted phenylsulfonyl chloride, the following compounds were prepared:

2-(4-Fluoro-benzenesulfonyl)-5-piperazin-1-yl-1,2,3,4-tetrahydroisoquinoline;
2-(4-Methoxy-benzenesulfonyl)-5-piperazin-1-yl-1,2,3,4-tetrahydroisoquinoline;
2-(3-Fluoro-benzenesulfonyl)-5-piperazin-1-yl-1,2,3,4-tetrahydroisoquinoline
2-(3,5-Dichloro-benzenesulfonyl)-5-piperazin-1-yl-1,2,3,4-tetrahydroisoquinoline;
2-(3,5-Bis-trifluoromethyl-benzenesulfonyl)-5-piperazin-1-yl-1,2,3,4-tetrahydroisoquinoline;
2-(2,5-dimethoxy-benzenesulfonyl)-5-piperazin-1-yl-1,2,3,4-tetrahydroisoquinoline;
2-(3-Chloro-4-fluoro-benzenesulfonyl)-5-piperazin-1-yl-1,2,3,4-tetrahydroisoquinoline;
2-(2-Fluoro-benzenesulfonyl)-5-piperazin-1-yl-1,2,3,4-tetrahydroisoquinoline;
2-(2-Chloro-benzenesulfonyl)-5-piperazin-1-yl-1,2,3,4-tetrahydroisoquinoline;
2-(3-Chloro-benzenesulfonyl)-5-piperazin-1-yl-1,2,3,4-tetrahydroisoquinoline;
2-(3-Methyl-benzenesulfonyl)-5-piperazin-1-yl-1,2,3,4-tetrahydroisoquinoline;
2-(2,3-Dichloro-benzenesulfonyl)-5-piperazin-1-yl-1,2,3,4-tetrahydroisoquinoline;
2-(2-Chloro-4-fluoro-benzenesulfonyl)-5-piperazin-1-yl-1,2,3,4-tetrahydroisoquinoline;
2-(2,5-Dichloro-benzenesulfonyl)-5-piperazin-1-yl-1,2,3,4-tetrahydroisoquinoline;
2-(2-Methanesulfonyl-benzenesulfonyl)-5-piperazin-1-yl-1,2,3,4-tetrahydroisoquinoline;
3-(5-piperazin-1-yl-3,4-dihydro-1H-isoquinoline-2-sulfonyl)-benzamide; and
[2-(5-piperazin-1-yl-3,4-dihydro-1H-isoquinoline-2-sulfonyl)-phenyl]-urea.

Using a procedure similar to that described above, and replacing the benzenesulfonyl chloride of Step 4 with the appropriate naphthalenesulfonyl chloride or quinolinyl sulfonyl chloride, the following compounds were prepared:
2-(Naphthalene-1-sulfonyl)-5-piperazin-1-yl-1,2,3,4-tetrahydroisoquinoline;
2-(Naphthalene-2-sulfonyl)-5-piperazin-1-yl-1,2,3,4-tetrahydroisoquinoline; and
8-(5-piperazin-1-yl-3,4-dihydro-1H-isoquinoline-2-sulfonyl)-quinoline.

Using a procedure similar to that described above, and replacing the 1-(tert-butoxycarbonyl)piperazine of step 2 with 4-methyl piperazine, the compound 2-Benzenesulfonyl-5-(4-methylpiperazin-1-yl)-1,2,3,4-tetrahydroisoquinoline was prepared.

Example 2

2-Benzyl-5-piperazin-1-yl-3,4-dihydro-2H-isoquinolin-1-one

The synthetic procedures described in this Example were carried out according to the process shown in Scheme E.

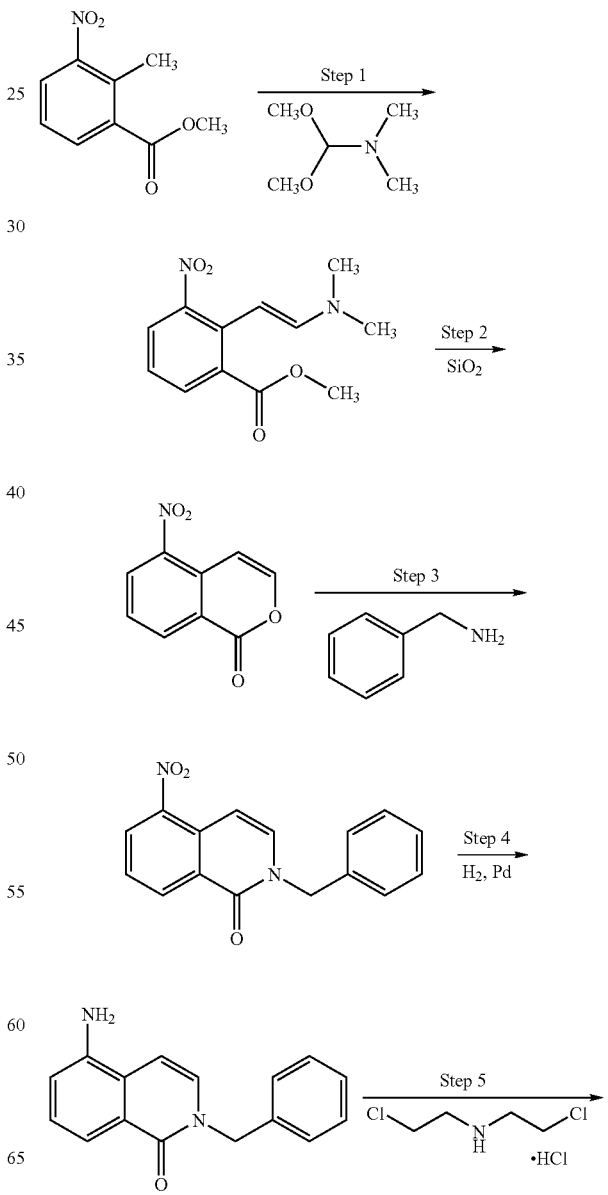

-continued

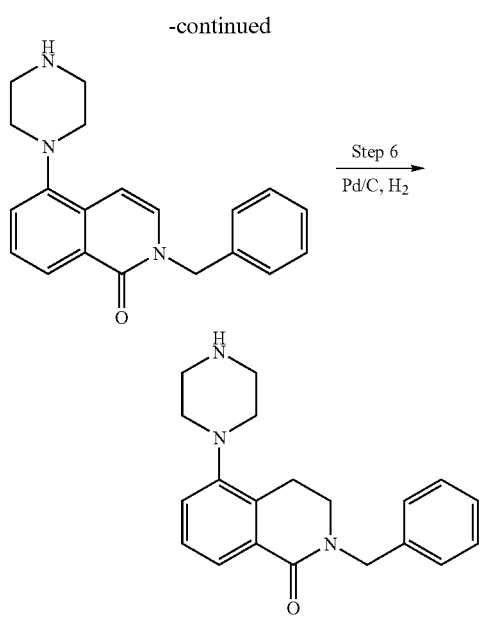

Step 6
Pd/C, H₂

The crude 2-(2-Dimethylamino-vinyl)-3-methyl-benzoic acid methyl ester of step 1 was subjected to silica gel chromatography (hexanes/EtOAc, 9:1) according to the procedure of Matsui et al., Supra, to afford 5-nitro-isochromen-1-one (2.7 g, 14.13 mmol) as a white solid.

Step 3

2-Benzyl-5-nitro-2H-isoquinolin-1-one

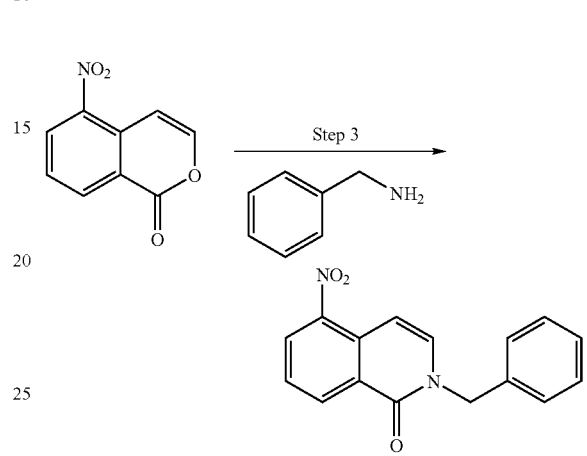

Step 3

5-Nitro-isochromen-1-one (1.0 g, 5.23 mmol) from step 2 was dissolved in excess benzylamine (5 mL) and heated to 80° C. for 4 hours. The mixture was then diluted in diethyl ether and washed several times with (0.5 N) HCl. The organic layer was concentrated in vacuo to give 2-benzyl-5-nitro-2H-isoquinolin-1-one as a yellow solid.

Step 4

5-Amino-2-benzyl-2H-isoquinolin-1-one

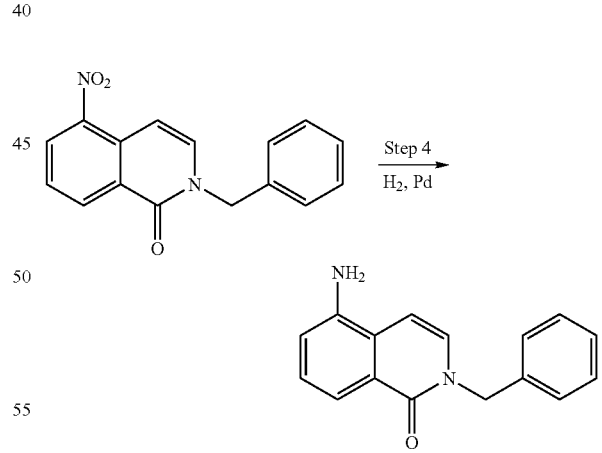

Step 4
H₂, Pd

Step 1

2-(2-Dimethylamino-vinyl)-3-methyl-benzoic acid methyl ester

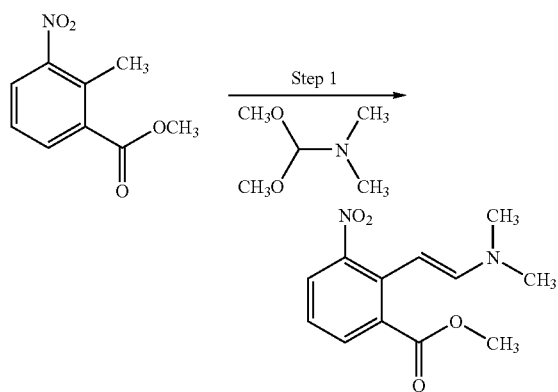

Step 1

2-Methyl-3-nitro-benzoic acid methyl ester (5.0 g, 25.6 mmol) was combined with dimethoxymethyl-dimethylamine (10.2 mL, 76.8 mmol, 3.0 eq.) and DMF (25 mL) and heated to 110° C. overnight. The reaction mixture was then concentrated in vacuo to yield crude 2-(2-Dimethylamino-vinyl)-3-methyl-benzoic acid methyl ester.

Step 2

5-Nitro-isochromen-1-one

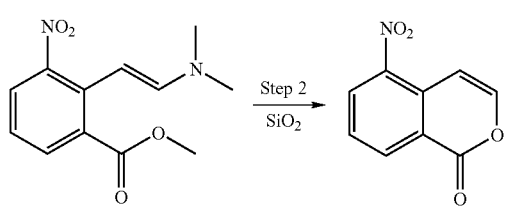

Step 2
SiO₂

2-Benzyl-5-nitro-2H-isoquinolin-1-one (1.0 g, 3.57 mmol) from step 3 was dissolved in 10 mL of EtOH, and a catalytic amount (50 mg) of 10% palladium on charcoal was added (under N₂ atmosphere). The vessel was then closed and exposed to hydrogen at 1 atmosphere for 2 hours. TLC indicated that reduction of the nitro group was complete after 1 hour, and the mixture was filtered and concentrated in vacuo to give 5-amino-2-benzyl-2H-isoquinolin-1-one (0.687 g, 2.75 mmol) as a pale yellow solid.

Step 5

2-Benzyl-5-piperazin-1-yl-2H-isoquinolin-1-one

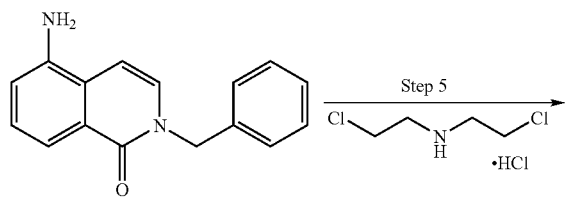

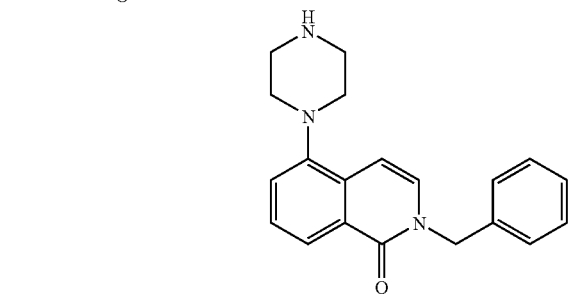

5-Amino-2-benzyl-2H-isoquinolin-1-one (0.687 g, 2.75 mmol)) from step 4 was combined with excess bis-(2-chloroethyl)-amine hydrochloride and heated to a melt for 5 minutes. TLC analysis showed one major product and several minor side products. The reaction mixture was chromatographed over silica gel ($CH_2Cl_2$/MeOH, 95:5) to afford 2-benzyl-5-piperazin-1-yl-2H-isoquinolin-1-one (0.103 mg, 0.32 mmol); M+H=320.

Step 6

2-Benzyl-5-piperazin-1-yl-3,4-dihydro-2H-isoquinolin-1-one

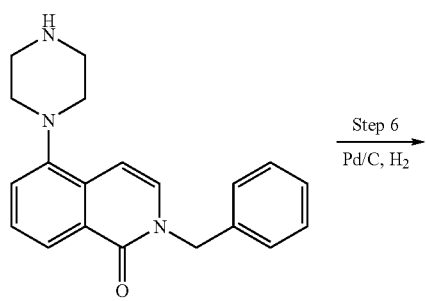

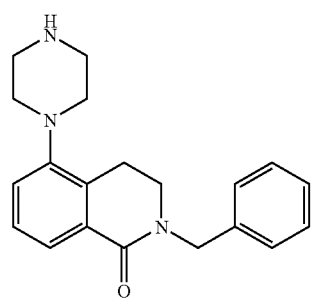

2-Benzyl-5-piperazin-1-yl-2H-isoquinolin-1-one (0.05 g, 0.16 mmol) from step 5 was added to a small (100 mL) Parr bottle, dissolved in 10 mL of EtOH, and a catalytic amount (25 mg) of palladium (10%) on charcoal was added (under $N_2$ atmosphere). The vessel was then exposed to 60 psig hydrogen for 24 hours. Preparative HPLC gave the desired product, 2-benzyl-5-piperazin-1-yl-3,4-dihydro-2H-isoquinolin-1-one (8 mg, 0.025 mmol); M+H=322.

The compound 2-benzyl-5-(4-ethyl-piperazin-1-yl)-3,4-dihydro-2H-isoquinolin-1-one (4 mg, 0.012 mmol); M+H=350, was also found as a product of the reduction of step 6 after analysis of preparative HPLC results.

Example 3

Formulations

Pharmaceutical preparations for delivery by various routes are formulated as shown in the following Tables. "Active ingredient" or "Active compound" as used in the Tables means one or more of the Compounds of Formula I.

Composition for Oral Administration

| Ingredient | % wt./wt. |
|---|---|
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration

| Ingredient | % wt./wt. |
|---|---|
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration

| Ingredient | Amount |
|---|---|
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation

| Ingredient | % wt./wt. |
| --- | --- |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation

| Ingredient | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation

| Ingredients | grams |
| --- | --- |
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025–0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50–100 microliters of formulation per actuation. A typical dosing schedule is 2–4 sprays every 4–12 hours.

Example 4

Radioligand Binding Studies

This example illustrates in vitro radioligand binding studies of compound of formula I.

The binding activity of compounds of this invention in vitro was determined as follows. Duplicate determinations of ligand affinity are made by competing for binding of [$^3$H]LSD in cell membranes derived from HEK293 cells stably expressing recombinant human 5-HT6 receptor. This cell line was prepared as described by Monsma et al., *Molecular Pharmacology*, Vol. 43 pp. 320–327 (1993).

All determinations were made in assay buffer containing 50 mM Tris-HCl, 10 mM MgSO$_4$, 0.5 mM EDTA, 1 mM ascorbic acid, pH 7.4 at 37° C., in a 250 microliter reaction volume. Assay tubes containing [$^3$H]LSD (5 nM), competing ligand, and membrane were incubated in a shaking water bath for 60 min. at 37° C., filtered onto Packard GF-B plates (pre-soaked with 0.3% PEI) using a Packard 96 well cell harvester and washed 3 times in ice cold 50 mM Tris-HCl. Bound [$^3$H]LSD was determined as radioactive counts per minute using Packard TopCount.

Displacement of [3H]LSD from the binding sites was quantified by fitting concentration-binding data to a 4-parameter logistic equation:

$$\text{binding} = \text{basal} + \left( \frac{B\text{max} - \text{basal}}{1 + 10^{-\text{Hill}(\log[\text{ligand}] - \log IC_{50})}} \right)$$

where Hill is the Hill slope, [ligand] is the concentration of competing radioligand and IC$_{50}$ is the concentration of radioligand producing half-maximal specific binding of radioligand. The specific binding window is the difference between the Bmax and the basal parameters.

Using the procedures of this Example, compounds of Formula I were tested and found to be selective 5-HT6 antagonists. The compound 2-(2,3-dichloro-benzenesulfonyl)-5-piperazin-1-yl-1,2,3,4-tetrahydroisoquinoline, for example, exhibited a pKi of 10.37 according to the above procedure.

Example 5

Cognition Enhancement

The cognition-enhancing properties of compounds of the invention may be in a model of animal cognition: the object recognition task model. 4-month-old male Wistar rats (Charles River, The Netherlands) were used. Compounds were prepared daily and dissolved in physiological saline and tested at three doses. Administration was always given i.p. (injection volume 1 ml/kg) 60 minutes before T1. Scopolamine hydrobromide was injected 30 minutes after compound injection. Two equal testing groups were made of 24 rats and were tested by two experimenters. The testing order of doses was determined randomly. The experiments were performed using a double blind protocol. All rats were treated once with each dose condition. The object recognition test was performed as described by Ennaceur, A., Delacour, J., 1988, A new one-trial test for neurobiological studies of memory in rats. 1: Behavioral data. *Behav. Brain Res.* 31, 47–59.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of the formula:

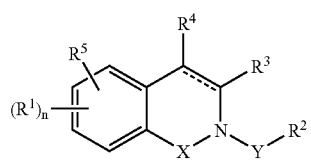

or a pharmaceutically acceptable salt,
wherein:
n is from 0 to 3;
X is —CR$^a$R$^b$— wherein R$^a$ and R$^b$ each independently are hydrogen or alkyl;
---- is an optional bond;
Y is —SO$_2$—;
each R$^1$ independently is halo, alkyl, haloalkyl, hydroxy, nitro, alkoxy, cyano, —S(O)$_q$—R$^e$, —NR$^c$R$^f$, or —C(=O)—NR$^c$R$^f$, wherein q is from 0 to 2 and R$^e$ and R$^f$ each independently are hydrogen or alkyl;
R$^2$ is phenyl or naphthyl optionally substituted with halo, alkoxy, haloalkyl, alkyl, or —C(O)—NH$_2$;
R$^3$ and R$^4$ each independently are hydrogen or alkyl; and
R$^5$ is at the 5- or 6-position of the isoquinoline ring system and is of the formula:

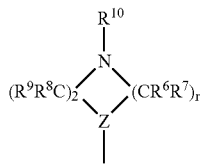

wherein:
Z is —N—;
r is 2; and
R$^6$, R$^7$, R$^8$, R$^9$ and R$^{10}$ each independently are hydrogen or alkyl.

2. The compound of claim 1, wherein R$^5$ is located at the 5-position of the isoquinoline ring system.

3. The compound of claim 1, wherein R$^a$ and R$^b$ are hydrogen.

4. The compound of claim 1, wherein R$^2$ is optionally substituted phenyl.

5. The compound of claim 1, wherein R$^2$ is optionally substituted naphthalenyl.

6. The compound of claim 4, wherein R$^2$ is selected from the group consisting of phenyl, 2-halophenyl, 3-halopheny, 4-halophenyl, 2,3-dihalophenyl, 2,4-dihalophenyl, 3,4-dihalophenyl, 2,5-dihalophenyl, 3,5-dihalophenyl, 2,6-dihalophenyl, 2-haloalkylphenyl, 3-haloalkypheny, 4-haloalkylphenyl, 2,3-dihaloalkylphenyl, 2,4-dihaloalkylphenyl, 3,4-dihaloalkylphenyl, 2,5-dihaloalkylphenyl, 3,5-dihaloalkylphenyl, 2,6-dihaloalkylphenyl, 2-alkoxyphenyl, 3-alkoxyphenyl, 4-alkoxyphenyl, 2,3-dialkoxyphenyl, 2,4-dialkoxyphenyl, 3,4-dialkoxyphenyl, 3,5-dialkoxyphenyl, 2,5-dialkoxyphenyl, 2,6-dialkoxyphenyl, 2-alkylphenyl, 3-alkylphenyl, 4-alkylphenyl, 2,3-dialkylphenyl, 2,4-dialkylphenyl, 3,4-dialkylphenyl, 3,5-dialkylphenyl, 2,5-dialkylphenyl, and 2,6-dialkylphenyl.

7. The compound of claim 5, wherein R$^2$ is naphthalene-1-yl or napthalene-2-yl.

8. The compound of claim 1, wherein n is 0.

9. The compound of claim 1, wherein R$^3$ and R$^4$ are hydrogen.

10. The compound of claim 1, wherein R$^6$, R$^7$, R$^8$, R$^9$ and R$^{10}$ are hydrogen.

11. The compound of claim 1, wherein R$^6$, R$^7$, R$^8$ and R$^9$ are hydrogen and R$^{10}$ is alkyl.

12. The compound of claim 1, wherein said compound is of the formula:

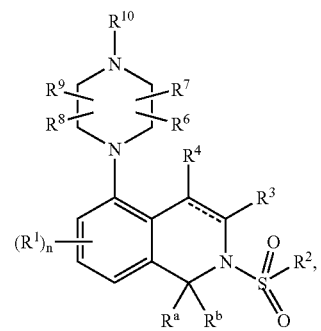

and wherein n, R$^1$, R$^2$, R$^3$, R$^4$, R$^6$, R$^7$, R$^8$, R$^9$, R$^{10}$, R$^a$ and R$^b$ are as defined in claim 1.

13. The compound-selected from the group consisting of:
2-benzenesulfonyl-5-piperazin-1-yl-1,2,3,4-tetrahydroisoquinoline;
2-benzenesulfonyl-5-(4-methylpiperazin-1-yl)-1,2,3,4-tetrahydroisoquinoline;
2-(4-fluoro-benzenesulfonyl)-5-piperazin-1-yl-1,2,3,4-tetrahydroisoquinoline;
2-(4-methoxy-benzenesulfonyl)-5-piperazin-1-yl-1,2,3,4-tetrahydroisoquinoline;
2-(3-fluoro-benzenesulfonyl)-5-piperazin-1-yl-1,2,3,4-tetrahydroisoquinoline;
2-(3,5-dichloro-benzenesulfonyl)-5-piperazin-1-yl-1,2,3,4-tetrahydroisoquinoline;
2-(3,5-bis-trifluoromethyl-benzenesulfonyl)-5-piperazin-1-yl-1,2,3,4-tetrahydroisoquinoline;
2-(2,5-dimethoxy-benzenesulfonyl)-5-piperazin-1-yl-1,2,3,4-tetrahydroisoquinoline;
2-(3-chloro-4-fluoro-benzenesulfonyl)-5-piperazin-1-yl-1,2,3,4-tetrahydroisoquinoline;
2-(2-fluoro-benzenesulfonyl)-5-piperazin-1-yl-1,2,3,4-tetrahydroisoquinoline;
2-(2-chloro-benzenesulfonyl)-5-piperazin-1-yl-1,2,3,4-tetrahydroisoquinoline;
2-(3-chloro-benzenesulfonyl)-5-piperazin-1-yl-1,2,3,4-tetrahydroisoquinoline;
2-(3-methyl-benzenesulfonyl)-5-piperazin-1-yl-1,2,3,4-tetrahydroisoquinoline;
2-(2,3-dichloro-benzenesulfonyl)-5-piperazin-1-yl-1,2,3,4-tetrahydroisoquinoline;

2-(2-chloro-4-fluoro-benzenesulfonyl)-5-piperazin-1-yl-1,2,3,4-tetrahydroisoquinoline;
2-(2,5-dichloro-benzenesulfonyl)-5-piperazin-1-yl-1,2,3,4-tetrahydroisoquinoline;
2-(naphthalene-1-sulfonyl)-5-piperazin-1-yl-1,2,3,4-tetrahydroisoquinoline;
2-(naphthalene-2-sulfonyl)-5-piperazin-1-yl-1,2,3,4-tetrahydroisoquinoline;
2-(2-Methanesulfonyl-benzenesulfonyl)-5-piperazin-1-yl-1,2,3,4-tetrahydroisoquinoline;
3-(5-Piperazin-1-yl-3,4-dihydro-1H-isoquinoline-2-sulfonyl)-benzamide; and
[2-(5-Piperazin-1-yl-3,4-dihydro-1H-isoquinoline-2-sulfonyl)-phenyl]-urea.

14. A compound of the formula:

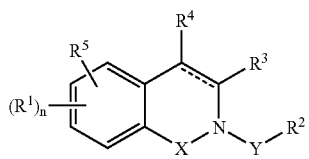

I or a pharmaceutically acceptable salt,
wherein:
n is from 0 to 3;
X is —$CR^aR^b$— wherein $R^a$ and $R^b$ each independently are hydrogen or alkyl;
---- is an optional bond;
Y is —$SO_2$—;
each $R^1$ independently is halo, alkyl, haloalkyl, hydroxy, nitro, alkoxy, cyano, —$S(O)_q$—$R^e$, —$NR^eR^f$, or —C(=O)—$NR^eR^f$, wherein q is from 0 to 2 and $R^e$ and $R^f$ each independently are hydrogen or alkyl;
$R^2$ is phenyl, 2-fluorophenyl, 3-fluorophenyl, 4-fluorophenyl, 2-chlorophenyl, 3-chlorophenyl, 3-methylphenyl, 4-methoxyphenyl, 2-methanesulfonylphenyl, 4-amidophenyl, 4-ureaphenyl, 3,5-dichlorophenyl, 2,3-dichlorophenyl, 2,5-dichlorophenyl, 3,5-di(trifluoromethyl)phenyl, 2,5-dimethoxyphenyl, 3-chloro-4-fluorophenyl, 2-chloro-4-fluorophenyl, naphthalen-1-yl, naphthalen-2-yl, or quinolin-8-yl $R^3$ and $R^4$ each independently are hydrogen or alkyl; and
$R^5$ is at the 5- or 6-position of the isoquinoline ring system and is of the formula:

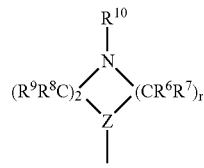

wherein:
Z is —N—;
r is 2; and
$R^6$, $R^7$, $R^8$, $R^9$ and $R^{10}$ each independently are hydrogen or alkyl.

15. A pharmaceutical composition comprising an effective amount of at least one compound of claim 1 in admixture with a pharmaceutically acceptable carrier.

16. A method for enhancing cognitive memory in an Alzheimer's patient said method comprising administering to said Alzheimer's patient a therapeutically effective amount of a compound of claim 1.

17. A method for producing a compound of claim 1, said method comprising:
reacting a compound of the formula:

wherein n, $R^1$, $R^a$, $R^3$, $R^4$ and $R^5$ are as recited in claim 1, with a sulfonyl halide of the formula: $R^2$—$SO_2$-G wherein G is halo and $R^2$ is as defined in claim 1;
to yield a compound of formula I wherein Y is —$SO_2$—.

* * * * *